US009849210B2

(12) United States Patent
Mohamed et al.

(10) Patent No.: US 9,849,210 B2
(45) Date of Patent: *Dec. 26, 2017

(54) DEVICES FOR EFFECTING FASTER HEALING OF ORTHOPEDIC AND OTHER WOUNDS

(71) Applicants: Hossam Abdel Salam El Sayed Mohamed, Ottawa (CA); Houda Abdul Rahman M. Al Mansour, Ottawa (CA)

(72) Inventors: Hossam Abdel Salam El Sayed Mohamed, Ottawa (CA); Houda Abdul Rahman M. Al Mansour, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,498

(22) Filed: Jan. 31, 2017

(65) Prior Publication Data
US 2017/0136142 A1    May 18, 2017

Related U.S. Application Data

(63) Continuation of application No. 13/936,580, filed on Jul. 8, 2013, now Pat. No. 9,579,414.

(51) Int. Cl.
*A61B 17/03* (2006.01)
*A61L 17/00* (2006.01)
(Continued)

(52) U.S. Cl.
CPC .......... *A61L 17/005* (2013.01); *A61B 17/064* (2013.01); *A61B 17/06166* (2013.01);
(Continued)

(58) Field of Classification Search
CPC ........ A61L 17/00; A61L 17/04; A61L 17/005; A61L 17/06; A61L 17/08; A61L 17/10;
(Continued)

(56) References Cited

U.S. PATENT DOCUMENTS 7,067,709 B2 * 6/2006 Murata ............... A61F 13/0203
602/41
8,252,333 B2 * 8/2012 Cueto-Garcia ......... A61L 15/28
424/425
(Continued)

FOREIGN PATENT DOCUMENTS

EP    2205292 B1    5/2013

OTHER PUBLICATIONS

Koshal et al., "Properties of Zinc-Oxide Eugenol" in "Impressions for Prosthetic Dentistry", University of Birmingham: The School of Dentistry, Accessed on Apr. 20, 2016 from http://www.dentistry.bham.ac.uk/cal/impress/znoeugd.htm.
(Continued)

*Primary Examiner* — Ahmed Farah
(74) *Attorney, Agent, or Firm* — Caesar Rivise, PC (57) ABSTRACT

Disclosed are medical devices, e.g., surgical sutures, surgical staples, surgical pads, surgical meshes, surgical scaffolds etc., and methods of use at a wound in a patient to facilitate the rapid healing of the tissue at the situs of the wound with minimal fibrous tissue formation. The devices are arranged to be brought into engagement with tissue adjacent the wound to close the wound and include a core formed of a piezo-electric material and an outer layer covering the core. The outer layer is platelet derived growth factors. The methods of use of the devices also include applying a local molecular energy production agent to the wound and irradiating the wound with a pulsed infra-red laser beam.

4 Claims, 4 Drawing Sheets

(51) Int. Cl.
  A61L 17/10   (2006.01)
  A61L 15/32   (2006.01)
  A61L 17/14   (2006.01)
  A61L 31/04   (2006.01)
  A61L 31/16   (2006.01)
  A61L 31/10   (2006.01)
  A61B 17/06   (2006.01)
  A61B 17/064  (2006.01)
  A61B 17/00   (2006.01)

(52) U.S. Cl.
  CPC .............. *A61L 15/32* (2013.01); *A61L 17/10* (2013.01); *A61L 17/145* (2013.01); *A61L 31/047* (2013.01); *A61L 31/10* (2013.01); *A61L 31/16* (2013.01); *A61B 2017/00884* (2013.01); *A61B 2017/00893* (2013.01); *A61B 2017/00964* (2013.01); *A61B 2017/06171* (2013.01); *A61L 2300/414* (2013.01); *A61L 2430/34* (2013.01)

(58) Field of Classification Search
  CPC .. A61L 17/145; A61L 17/0401; A61L 17/064; A61L 17/0642; A61L 17/0643; A61L 17/0644; A61L 17/083
  USPC ... 606/1, 53, 54, 75–77, 139, 151–154, 157, 606/213, 215, 216, 219, 221, 228–231
  See application file for complete search history.

(56) References Cited

U.S. PATENT DOCUMENTS

| | | | | |
|---|---|---|---|---|
| 9,233,028 B2* | 1/2016 | Pratt | ................ | A61F 13/00068 |
| 9,579,414 B2* | 2/2017 | Mohamed | ........ | A61B 17/06166 |
| 9,789,303 B2* | 10/2017 | Mower | ................ | A61N 1/0468 |
| 2004/0101819 A1* | 5/2004 | Montemagno | ....... | C12N 5/0658 435/4 |
| 2010/0198257 A1 | 8/2010 | Stopek et al. | | |
| 2012/0071566 A1 | 3/2012 | Kelly et al. | | |
| 2012/0179176 A1* | 7/2012 | Wilson | ................... | A61F 2/0063 606/151 |
| 2012/0239161 A1 | 9/2012 | Datta et al. | | |
| 2013/0115457 A1* | 5/2013 | Haynie | ................... | D01D 5/003 428/401 |
| 2014/0227228 A1* | 8/2014 | Asolkar | ................. | A01N 63/02 424/93.4 |
| 2014/0371767 A1* | 12/2014 | Ostapoff | ................ | A61L 17/105 606/151 |

OTHER PUBLICATIONS

Morgan Advanced Materials, "Chapter 2.1 The piezoelectric effect in ceramic materials" in "Piezoelectric Ceramics Properties and Applications", Accessed on Apr. 20, 2016 from www.morgantechnicalceramics.com/sites/default/files/documents/chapter2_1_pdf.

Komarcevic, Abstract of "The Modern Approach to Wound Treatment", Medicinski Pregled, Jul.-Aug. 2000, vol. 53, issue 7-8, pp. 363-368.

International Search Report for PCT/IB2013/001520 dated Oct. 8, 2013.

Oxford Reference Overview entitled "Zinc Oxide Eugenol Impression Paste" downloaded from http://www.oxfordreference.com/view/10.1093/oi/authority.20110803133505822 on Jul. 7, 2017, 1 page.

Boston Piezo-Optics Inc. article entitled "Intro to Piezoelectric Transducer Crystals" downloaded from http://www.bostonpiezooptics.com/intro-to-transducer-crystals on Jul. 6, 2017, pp. 1-7.

* cited by examiner

DEVICES FOR EFFECTING FASTER HEALING OF ORTHOPEDIC AND OTHER WOUNDS

CROSS-REFERENCE TO RELATED APPLICATIONS

This application is a continuation of application Ser. No. 13/936,580, filed on Jul. 8, 2013, entitled DEVICES AND METHODS FOR EFFECTING FASTER HEALING OF ORTHOPEDIC AND OTHER WOUNDS, the entire disclosure of which application is specifically incorporated by reference herein.

FIELD OF THE INVENTION

This invention relates generally to medical devices and methods of use and more particularly to devices and methods of use for expediting healing of orthopedic and other wounds.

BACKGROUND OF THE INVENTION

The orthopedic wound is one of worst wound because it is usually deep towards bone surface. It necessitates cutting of the skin, subcutaneous tissues, and all the muscle layers down to the bone. Therefore, it is associated with many complications such as ugly skin scar, delayed healing, wasting of the limb, post-operative infection, and/or functional loss due to damage of vital structures like blood vessels or nerves.

All tissues of human body, except bone, heal by different degrees of fibrosis. The bone is the only tissue/structure that is not allowed to heal, except by bone similar to original one. Healing of a bone fracture with some degree of fibrosis is considered as a pathological process. It is clinically presented as either non-union or delayed union according to the amount of fibrous tissues. If a little amount of fibrous tissues is associated with healing, it is called as delayed union. If a large amount of fibrous tissues is associated with healing, it is called non-union, which usually necessitates surgical intervention. The effect of presence of fibrous tissues on bone healing is a tendency to fracture again.

A bone's function is to support all other structures so it is needed to be strong tissue and any area of fibrosis acts as a weak point subsequently, concentrating the stress to that point resulting in a re-fracture with minimal trauma. This phenomenon is known biomechanically as a stress raiser. Bone has two main properties that differentiate it from all other tissues in the human body. First, it has the largest number of mesenchymal cells (MSCs) in the bone marrow. These cells have the capacity to repair the damaged tissues with new ones similar to the original surrounding structure. This is the basis of stem cells injection for repairing of the tissues. Since 2009, it is well established that these MSCs are present in a dormant state around the blood vessels in all human tissues. The second property is that bone has a piezo-electric characteristics, e.g., compressing a living bone will produce electrical current of approximately $10^{-14}$ volts. This piezo-electrical property is fundamental for both bone maintenance and healing of a bone fracture. The electrical current acts as a method of cell-to-cell communications for new bone formation proportional to the amount of the mechanical stress. In other words, the higher mechanical stress on the bone, the higher the electrical charge produced. This action results in stimulation of more cells causing more new bone formation. The reverse is also true. In other words, it is both a proportional and quantitative process.

Recent research, in case of bone fracture, showed that this electrical charge stimulates dormant MSCs to be converted to bone cells Moreover, the site of fracture acts as a focusing site of the mechanical stresses which further enhance the stimulation of MSCs to become bone cells (osteoblasts which will become mature osteocytes). These cells are responsible of healing without fibrous tissues because the healing process is generated by MSCs not by fibroblast like other tissues.

To sum up, bone is unique tissue for the following reasons. First, it has the highest number of MSCs relative to other tissues (where the MSCs are present only around blood vessels). Being a piezo-electrical material, bone is capable of stimulating dormant MSCs. A fracture in a bone is the site of focussed mechanical stresses. Those stresses are also able to stimulate MSCs, since MSCs are very sensitive to mechanical stimuli. Therefore, MSCs have double stimulants, namely, electrical and mechanical ones. The above reasons are responsible for the normal bone healing without fibrous tissues formation, because healing is done with MSCs.

Heretofore wounds to tissue other than bone have not exhibited the same response of healing as a bone injury. Thus, wounds particularly severe wounds, like orthopedic wounds, are frequently slow to heal and result in substantial fibrosis formation. The so-called "soft tissue healing law" is, perhaps, one of the most important paradigms in soft tissue healing and clearly denotes that the speed of the healing process is inversely proportional to the amount of the fibrous tissue formation. As such, there is a continuous and progressive need for faster healing of soft tissue wounds with less fibrous tissues. Such a result is desirable for both cosmetic and functional reasons, e.g., to regain the shape and function of any organ to its baseline condition just before it became wounded.

Moreover, the healing process is enhanced by an increased blood supply and the local molecular energy production, while it is inhibited by presence of infection and/or extensive tissue damage. In accordance with the soft tissue healing law, reducing the amount of fibrosis to a minimum enables the healing process to be indirectly increased to highest level.

Thus, the need exists for devices and methods for facilitating the rapid healing of wounds other than bone (e.g., soft tissue wounds of skin, muscle, tendon, etc.) with minimal, if any, fibrosis.

The subject invention addresses that need.

SUMMARY OF THE INVENTION

In accordance with one aspect of the invention, there is provided a medical device, selected from the group consisting of surgical sutures, surgical staples, surgical pads, and surgical meshes, for use at a wound in a patient to facilitate the rapid healing of the tissue at the situs of the wound with minimal fibrous tissue formation. The device is a member that is arranged to be brought into engagement with tissue adjacent the wound to close the wound. The device comprises a core formed of a piezo-electric material and an outer layer covering the core. The outer layer comprises platelet derived growth factors.

In accordance with another aspect of this invention there is provided a method for closing a wound in a patient to facilitate rapid healing of the wound with minimal fibrous tissue formation. The method basically entails providing a suture or staple comprising a core formed of a piezo-electric material and an outer layer covering said core. The outer layer comprises platelet derived growth factors. The suture or staple is used to bring portions of tissue of the patient contiguous with the wound into engagement with each other to close the wound. Subsequent movement of the patient, e.g., naturally occurring activity, by the patient causes said piezo-electric material to produces an electrical current stimulating or activating MSCs in adjacent tissue.

In accordance with one preferred aspect of the method of this invention a local molecular energy production agent, e.g., glutamine-creatine complex, is applied to the wound.

In accordance with another preferred aspect of the method of this invention a pulsed infra-red laser beam is applied to the wound.

DETAILED DESCRIPTION OF THE PREFERRED EMBODIMENT

Figures 1, 2A, 2B:
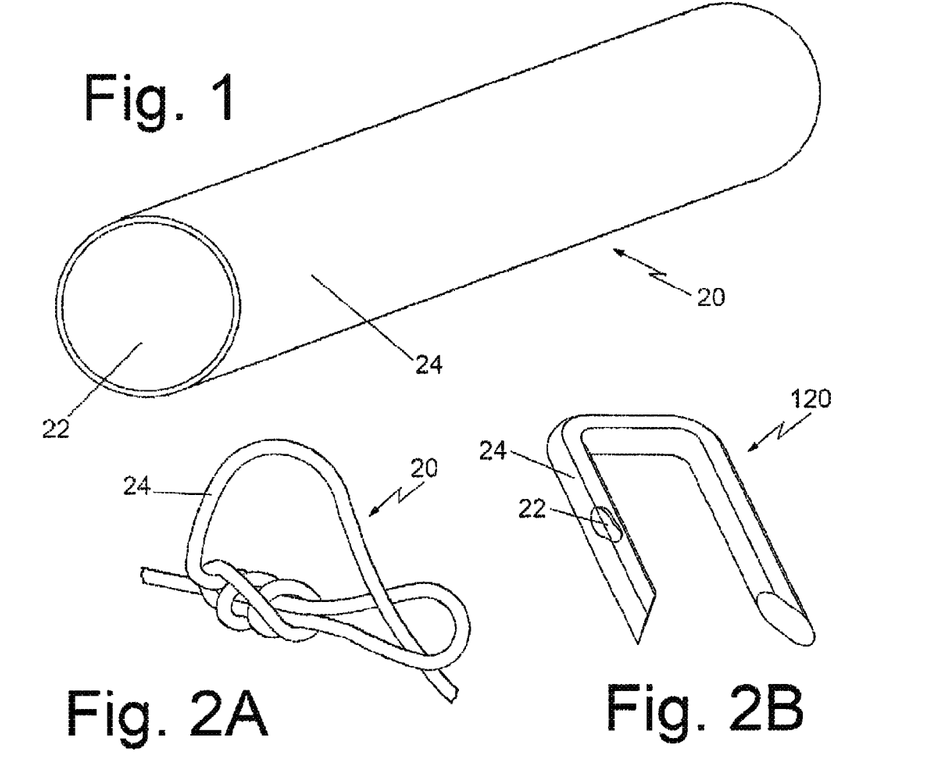
FIG. 1 is greatly enlarged isometric view of a section of a surgical suture, constructed in accordance with this invention.
FIG. 2A is a reduced isometric view of a surgical suture constructed in accordance with this invention.
FIG. 2B is a reduced isometric view of a surgical staple constructed in accordance with this invention.
Figure 2C:
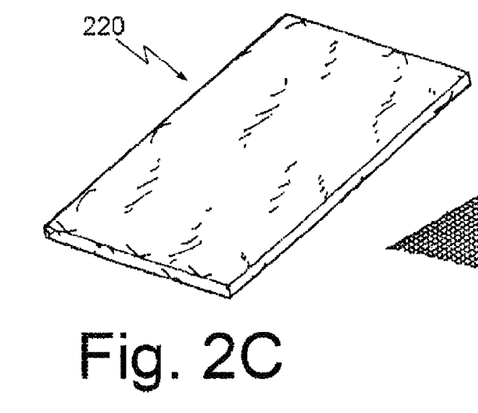
FIG. 2C is a reduced isometric view of a surgical skin pad constructed in accordance with this invention.
Figure 2D:
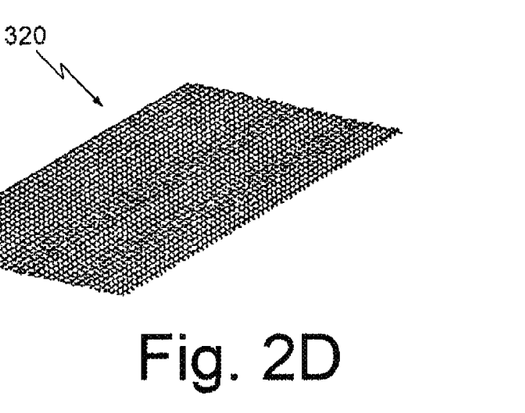
FIG. 2D is a reduced isometric view of a surgical mesh or surgical scaffold constructed in accordance with this invention.
Figure 3:
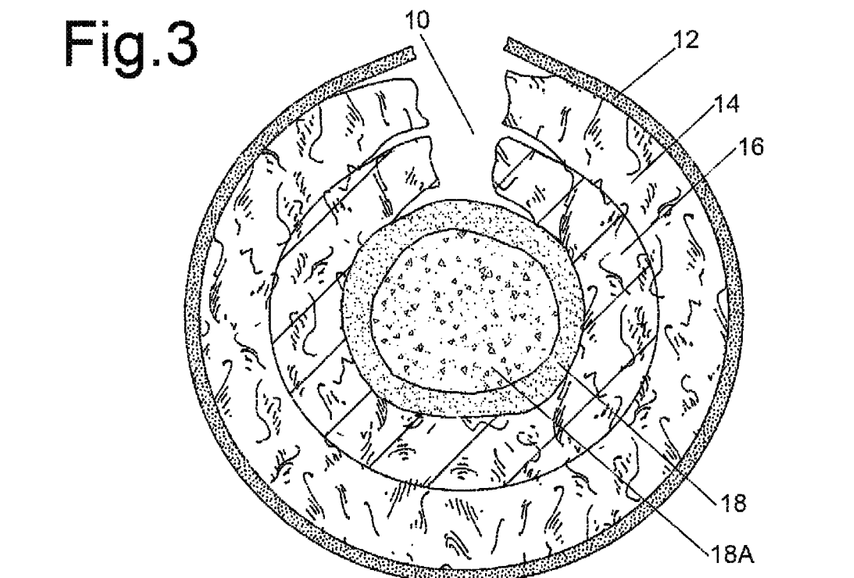
FIG. 3 is an illustration, in cross-section, of an exemplary deep orthopedic wound to be treated and healed in accordance with this invention.

Referring now to the various figures of the drawing wherein like reference characters refer to like parts, there is shown at 20 in FIGS. 1 and 2A a section of a surgical suture constructed in accordance with one aspect of this invention. The suture 20 is just one of several devices constructed in accordance with this invention to facilitate rapid wound healing without fibrosis. In particular, the subject invention contemplates staples 120 (such as shown in FIG. 2B), surgical pads (such as shown in FIG. 2C), surgical meshes or surgical scaffolds (such as shown in FIG. 2D), and any other devices that could be used to facilitate a wound's closure and healing. All of the devices of this invention share a common attribute, namely, they are formed of piezo-electric material core, which is covered by a thin layer or cortex of platelet derived growth factors (PDGF). The details of their construction and the usage of them to treat a wound in accordance with methods aspects of this invention will be described later.

At this time a brief background of the technology involved is in order. To that end, experimental studies of the utilization of piezo-electric materials for repairing surgical and non-surgical wounds give very promising results. The results show reduction of fibrosis to a minimum. The explanation is that the piezo-electric material that repairs the wound when mechanically stimulated produces electrical current that is capable of activating dormant MSCs surrounding the blood vessels. This action results in healing of each tissue by the same original tissue surrounding the MSCs. e.g. muscle heals by muscle, tendon heals by tendon, and skin heals by skin, and so on.

The utilization of stem cells injection to reduce fibrosis and accelerate healing for both surgical and non-surgical wounds is expensive and unpractical. The subject invention, by making use of piezo-electric materials, helps to stimulate the production of those cells without the need for stem cell injections.

Other factors which help to reduce fibrosis and subsequently accelerate the healing process are increasing the blood supply to the wound. The more blood is supplied to the wound, the faster the healing and the faster the healing the less the fibrous tissues are formed. This can be done by external application of infra-red laser therapy to the wound on daily basis in the post-operative period of wound care.

Local molecular energy production also has a beneficial effect on wound healing. Such energy production can be increased by the addition of glutamine-creatine complex to the cavities of the wound since glutamine-creatine complex acts as an available local source of energy. Enhanced local energy production is the most important factor for reducing the amount of tissue damage and accelerating the process of healing (this is active process which needs fuel and glutamine-creatine complex can be considered as the best source of that fuel). Thus, enhancing energy production will subsequently reduce fibrosis.

The presence of infection is clearly counterproductive to wound healing and results in the formation of fibrous tissue. The infection may be clinical (e.g., manifested by redness, hotness, fever, pain, etc.) or sub-clinical (not obvious clinically). The higher the degree of infection, the more the fibrous tissue is formed, because infection delays the healing process and delayed healing is associated with more fibrosis. This step can be achieved by being strictly adherent to all appropriate antiseptic measures.

Lastly, the more severe the wound, e.g., damage to adjacent tissue, the more likely the fibrosis will result. This occurs because tissue damage results in a devitalized area, which acts as tissue debris subsequently delaying the healing process and thereby leading to more fibrous tissue formation.

In accordance with this invention fibrosis can be reduced to a minimum by strictly adherence to the following guide lines. First, activation of MSCs should be encouraged so that the healing process would depend mainly on them, not on fibro-blast like all other tissues except the bone. Activation of MSCs can be achieved by mechanical, electrical, and thermal (e.g., by infra-red (IR) laser) as will be explained later. Second, the local application of substances, e.g., the heretofore identified glutamine-creatine complex, to supply the tissues with energy sufficient for reconstruction (which logically is higher than the energy needed for tissue maintenance of the baseline resting state) should be undertaken. Third, enhancement of the local blood supply, e.g., via the application of IR laser energy, should be undertaken. Fourth, infection, even subclinical infection, should be eliminated or kept to an absolute minimum by strictly adherence to all suitable antiseptic measures. Fifth, the extent of tissue damage should be kept to a minimum during surgery or treatment by minimizing tissue dissection to the appropriate extent possible and reducing the time of surgical intervention as possible. Sixth, in case of a chronic wound, debridement of the wound by removal of all devitalized tissues (which are full of fibrous tissues) should be undertaken. Such action will leave fresh tissues, which have a better capacity to heal rapidly without fibrosis.

To accomplish the foregoing guidelines the subject invention makes a use of a regimen of three components. They are: (1) usage of specifically designed biologic materials, e.g., sutures, staples, pads, meshes, etc., for repairing the wound, (2) usage of local molecular energy production agents, e.g., glutamine-creatine complex, in the wound, and (3) enhancement of blood, oxygenation, and stimulation of dormant MSCs, immune cells and unwound DNA by the application of IR laser energy to the wound.

With respect to the specifically designed biologic materials component of the subject invention, such components all make use of a piezo-electric material as a core of a suture or staple or as a filament or some other structure making up a surgical pad, surgical mesh or surgical scaffold.

Covering the core is a thin layer or cortex of platelet derived growth factors (PDGF). Those materials form the biological substance used for repair of the wound, e.g., sutures constructed in accordance with this invention can be used for repairing muscle, while staples constructed in accordance with this invention can be used for repairing skin. Biological meshes or scaffolds using fibers or some other structures constructed in accordance with this invention, e.g., having a piezo-electric core and a PDGF outer layer, can be used for repairing tissue defects. Biological skin pads making use of a piezo-electric core and a PDGF outer layer can be used as a dressing on the wound. Thus, in accordance with one aspect of this invention piezo-electric material is used as a core substance for everything used to repair the wound e.g. sutures, staples, tissue pads, meshes, scaffolds, and so on.

FIG. 1 is a greatly enlarged isometric view of a suture 20 constructed in accordance with one aspect of this invention. FIG. 2A is a reduced isometric view of that suture. Thus, as can best be seen in FIG. 1 the suture 20 basically comprises a flexible core 22 formed of any suitable piezo-electric material. To that end, the material should fulfill the following criteria. It must be sufficiently strong to resist the tensile stresses, like conventional sutures. It must be pliable and bendable without any fissuring or fracture when the suture rotates around the split tissues in the process of suturing. It must be an inert material or at least not react negatively with the tissues to facilitate either inflammation or infection. The total outside diameter of the suture, i.e., the core and cortex, must match the conventional suture diameters e.g. sutures of thick and strong fasciae or muscles are usually thicker than those of the skin sutures.

The following are some examples of piezo-electric materials fulfilling those criteria: diphenylalanine peptide, polyvinylidene fluoride (PVDF), and zinc oxide. As is known diphenylalanine peptide is a pseudo-amino acid meaning similar to amino-acid phenylalanine and alanine. It does not harm the tissues and it is absorbed by the body within two months when soft tissues have fully healed. Polyvinylidene fluoride (PVDF) is polymer substance which is inert and doesn't react with human tissue. Zinc oxide is a substance that can be re-absorbed by the human body with two months and it is beneficial for human body. The above examples are not exclusive. Thus, other suitable piezo-electric materials may be used.

Surrounding the core is a thin layer or cortex 24 of PDGF. The piezo-electric core 22 can be of any suitable cross-section and size, depending upon the desired diameter of the suture. Obviously, some sutures will be of greater diameter than others, depending upon the surgical application. In any case, it is preferred that the diameter of the core be approximately ⅚ of the thickness of the diameter of the suture, e.g., the core and the cortex. Thus, the thickness of the PDGF cortex is approximately ⅙ of the diameter of the suture. While the above ratio of the core to the cortex is preferred other ratios are contemplated by this invention.

FIG. 2B is an isometric view of a staple 120 constructed in accordance with this invention. Thus, like the suture 20 it is made up of a piezo-electric core 122 which is covered by a thin layer 124 of PDGF. The core 122 can be of any suitable cross-section and size to be consistent with conventional staples. Staples, meshes and scaffolds constructed in accordance with this invention should be stronger and not pliable or bendable like suture material. This can be achieved by hardening of the polyvinylidene fluoride, the diphenylalanine peptide, or the zinc oxide material by adding quartz to it. Quartz itself is also a piezo-electric material. Like the suture, the thickness of the outer layer 124 of the staple 120 is approximately ⅙ of the diameter or cross-section of the staple.

FIG. 2C is an isometric view of a surgical pad 220 constructed in accordance with this invention. The pad can be made up of numerous fibers, each of which includes a piezo-electric core which is covered by a thin layer of PDGF. Alternatively, the pad can be a sheet of core material which is covered by a thin layer of PDGF.

FIG. 2D is an isometric view of a surgical mesh 320 constructed in accordance with this invention. The mesh or scaffold can be made up of an array or lattice of numerous fibers, each of which includes a piezo-electric core which is covered by a thin layer of PDGF, or can be of any other suitable construction so long as it includes a piezo-electric core which is covered by a thin layer of PDGF.

In should be point out at this juncture that it is contemplated that the subject invention may make use of other materials than PDGF for the outer layer over the piezo-electric core, providing that such outer layer materials provide the same effects and benefits as PDGF.

FIGS. 3-7 show one preferred method of closing and treating a substantial orthopedic wound using sutures 20 and staple 120 constructed in accordance with this invention to effect the rapid healing of the wound with minimal fibrosis. The steps of that methodology will be described in detail shortly. However, before doing so it should be pointed out that irrespective of what type of component constructed in accordance with this invention, be it a suture, staple, pad or mesh, is used in or on the wound, the mechanical stimulation of the piezo-electric material caused by normal activities of the patient, will lead to the production of electric current by the piezo-electric material. Recent studies show that the electrical current is more or less proportional to degree of mechanical stress which causes healing to be in harmony with stress, exactly like what happens in bones. In other words, the area of higher stress has more new tissue formation than that of lesser stress. Therefore, this method of healing is considered biomechanically more physiological healing. Moreover, the electrical current produced will activate dormant MSCs in the wound so that healing will occur and the newly formed tissue will be similar to that surrounding the wound, e.g., skin heals by skin, muscle heals by muscle, and tendon heals by tendon, etc.

The platelet derived growth factors (PDGF), which forms the thin cortex, sleeve or layer around or covering the thick piezo-electric core, is slowly released into the substance of the wound throughout the healing process. As is known PDGF can dramatically reduce pulmonary and hepatic fibrosis. PDGF also stimulates faster tissue healing. In this regard, some studies show that PDGF repairs the damaged tissues that could not be repaired even by surgical intervention.

With respect to the usage of local molecular energy production agents, e.g., glutamine-creatine complex, in the wound, this invention contemplates that such materials will be used for lavage of the wound and filling the cavities of fascial planes. The glutamine-creatine complex greatly accelerates the healing process and reduces the fibrous tissue formation. In this regard, extensive studies and research has shown that direct applications of glutamine-creatine complex into the cavities of the wounds give unexpected marked rapid healing with minimal fibrous tissue formation. Our understanding of molecular mechanic of soft tissue healing of the wound gives us better analysis of the effect of this complex on healing process. In this regard, the mechanics of soft tissue wound healing include the following. The wound acts as a stress which needs more blood supply for the process of reconstruction. In fact, the healing process needs more oxygen and glucose as a main source of energy than normal tissue maintenance. Since any wound will result in cutting of adjacent blood vessels and a concomitant reduction in the supply of both oxygen and glucose needed for healing, healing is retarded. In other words, the source of energy for the healing process is less than that used for maintenance in the resting state and this is the main cause for delayed healing processes and subsequent fibrosis.

The usage of glutamine-creatine complex can reverse the above mechanism by accelerating the healing process by the availability of the alternatives source of energy for healing. Recent studies show that glutamine can give energy without need of glucose by its entrance directly into Kerb's cycle. On other hand, creatine can supply energy to the tissues in the absence of oxygen. This clearly denotes that energy necessary for healing process becomes readily available even in shortage of both glucose and oxygen. As mentioned above, faster healing means a reduction in fibrosis formation. Glutamine is the commonest amino acid in human blood and is considered the best source of energy for all tissues. Glutamine is an alkaline medium that neutralizes the acidity that is present in all types of tissue damages, like wounds. Acid medium inhibits tissue growth and healing while, alkaline medium does the opposite. Moreover, alkaline medium also activates some enzymes necessary for healing, e.g., alkaline phosphatase enzyme necessary for bone healing.

In the case of diabetes, glucose is elevated, but the tissues cannot utilize it as a source of energy that is necessary for healing. Therefore, local glutamine-creatine usage has the beneficial effect by production of a much larger amount of energy necessary for healing without dependence on glucose or oxygen. As is known glutamine is de-aminated to α-ketoglutarate that readily enter Kerb's cycle for energy production, while creatine give much energy through an anaerobic pathway.

Creatine helps build muscle mass by making energy to be readily available so improve the muscles performance.

Recent researches confirmed that injection of glutamine-creatine complex in ischaemic deep seated structures gives excellent results of rapid healing of these tissues that were refractory to most methods of treatment. The molecular explanation is that glutamine-creatine complex gives energy to the ischemic tissues helping their repair. Moreover, glutamine and creatine are separately weak activators of MSCs, but the combination acts as strong stimulant of MSCs.

Thus, use of glutamine-creatine complex as a lavage and as an insert into the tissue cavities at the wounds, e.g., between muscle planes (as will be described later) should foster healing with minimal fibrosis.

The usage of pulsed IR laser energy to the wound after it has been closed and with sutures, staples, pads and/or meshes, constitutes another aspect of this invention in order to enhance the healing process. Thus, it is contemplated that such IR laser energy will be applied each day (or on whatever schedule is deemed particularly appropriate for the particular wound and patient). Pulsed IR laser energy can penetrate tissue to a depth of up to three inches and has the effect of increasing the local blood supply to the tissues, increasing tissue oxygenation, stimulating of dormant MSCs, stimulating immune cells (e.g., lymphocytes and macrophage) to clean tissue debris which delay healing with subsequent fibrosis, and stimulating of DNA double helix to be in an unwounded position, thereby increasing protein synthesis Turning now to FIG. 3, there is shown in cross section a deep orthopedic wound. In particular, it can be seen that the wound 10 extends through the skin and subcutaneous tissue layer (collectively designated by the reference number 12), through the outer muscle layer 14, the inner muscle layer 16 down to the bone 18. The bone cavity medulla is designated as 18A. This wound is typical of an orthopedic incision routine in joint replacement, reconstruction of peri-articular fractures, treatment of osteomyelitis, treatment of bone tumor, and bone biopsy.

Figure 4:
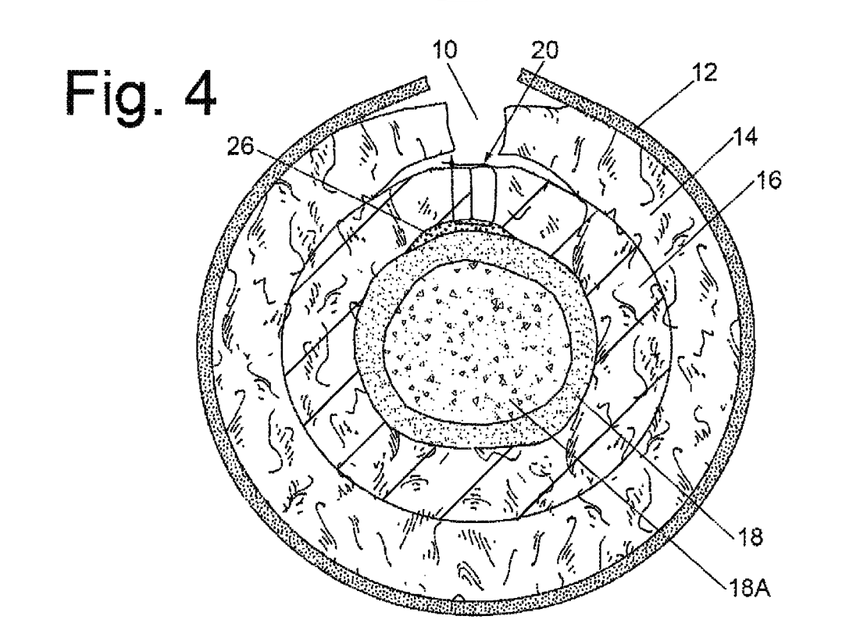
FIG. 4 is an illustration, similar to FIG. 3, showing an initial step in the treatment and healing of the wound using surgical sutures and staples constructed in accordance with this invention.

As a first step in the procedure a lavage of the wound by means of glutamine-creatine complex is undertaken. In particular, as shown in FIG. 4, which represents a wound resulting from a joint replacement or condylar fracture repair, after the lavage glutamine granules 26 are filled in the deep tissue plane. The deep (inner) muscle portions contiguous with the wound are sutured to each other with sutures 20, like that described above, i.e., suture having a piezo-electric core and a thin PDGF cortex.

Figure 5:
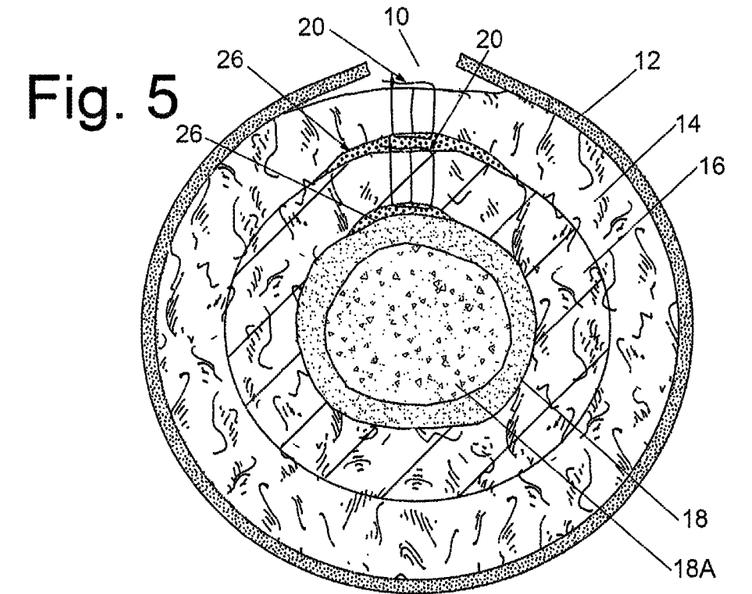
FIG. 5 is an illustration, similar to FIGS. 3 and 4, showing a subsequent step in the treatment and healing of the wound using surgical sutures and staples constructed in accordance with this invention.
Figure 6:
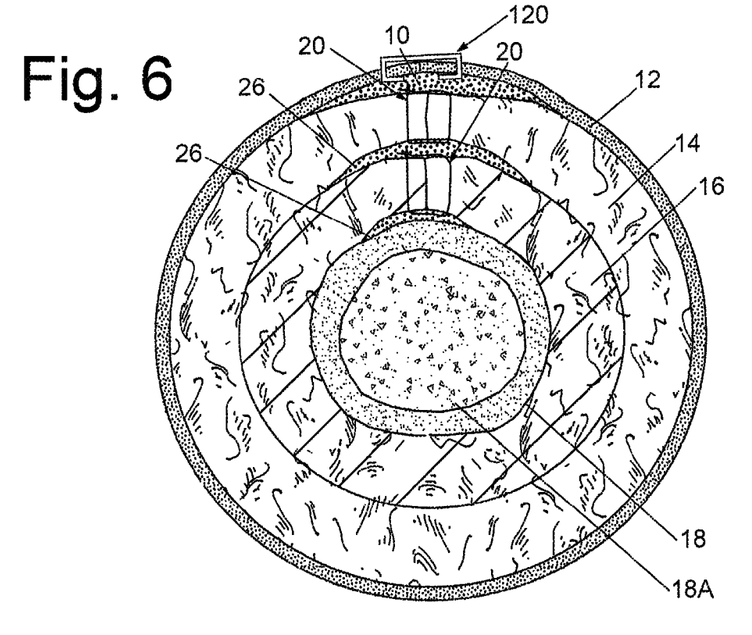
FIG. 6 is an illustration, similar to FIGS. 3-5, showing a still further step in the treatment and healing of the wound using surgical sutures and staples constructed in accordance with this invention.

The next step in the procedure is shown in FIG. 5, wherein glutamine-creatine complex granules 26 are filled in the tissue plane between the inner muscles and the outer (superficial) muscles 14. The outer or superficial muscle portions 14 contiguous with the wound are sutured to each other with other sutures 20 constructed in accordance with this invention. Once that has been accomplished the cavity in the tissue plane between the superficial muscles and the subcutaneous tissue layer is filled with glutamine-creatine complex granules 26. The marginal edges of the skin and subcutaneous tissue 12 are then brought together and stapled using staples 120 constructed in accordance with this invention, i.e., having a piezo-electric core and a thin PDGF outer layer.

Figure 7:
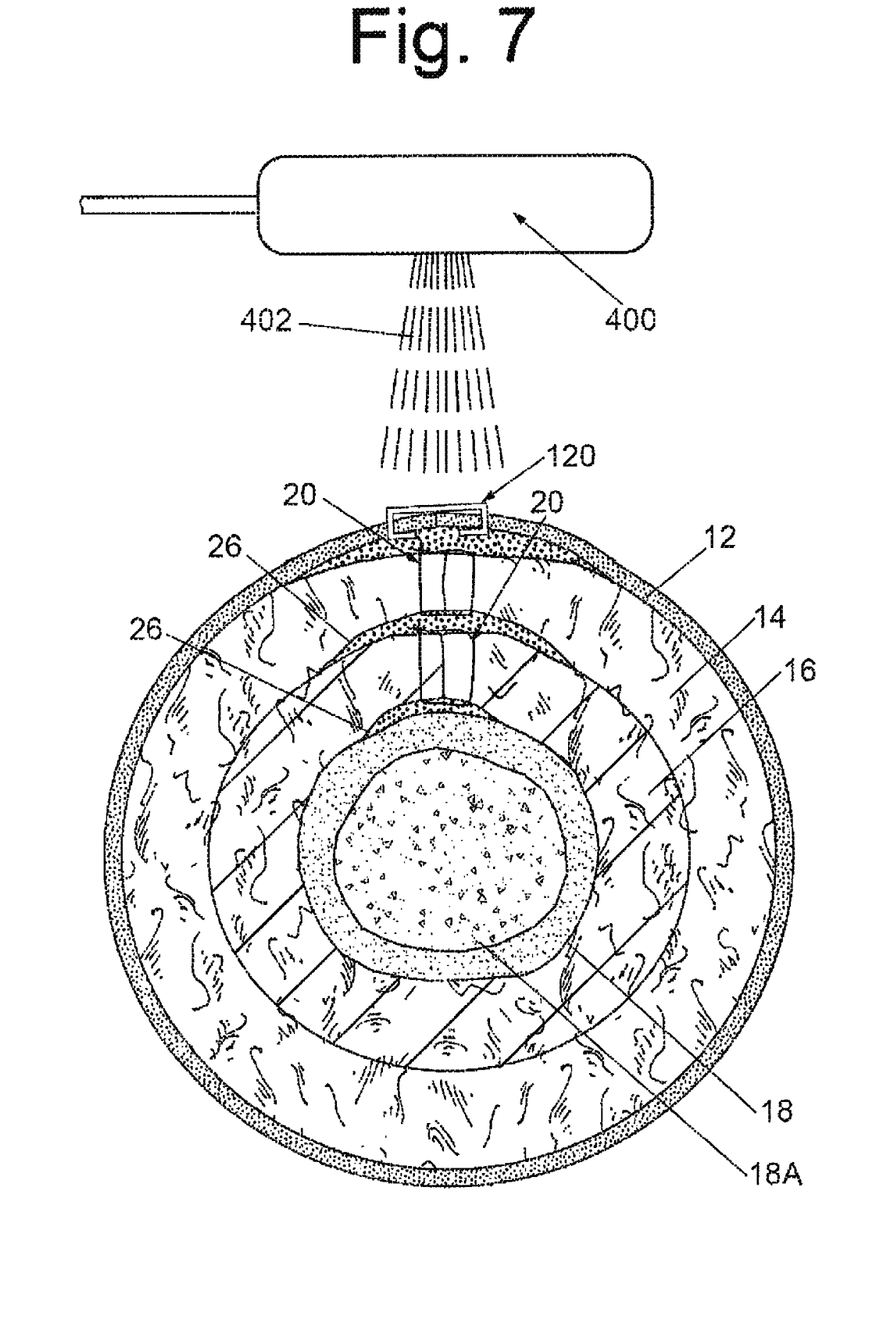
FIG. 7 is an illustration, similar to FIGS. 3-6, showing the last step in the treatment and healing of the wound using surgical sutures and staples constructed in accordance with this invention.

After closure of the wound as just described, it is preferably subjected to pulse IR laser energy. This action is shown in FIG. 7. To that end a pulse IR laser 400 is juxtaposed over the closed wound and operated to produce a pulsed IR laser beam 402 which is directed to the closed wound. As is known, there are three basic types of IR radiation, namely: Far Infra-red (FIR), Mid infra-red (MIR), and Near infra-red (NIR). NIR can be absorbed by pigmented structures of human bodies including hemoglobin, chromosomes of the nucleus, and cytochrome oxidase enzymes of the mitochondria. FIR facilitates new bone formation. In particular, FIR stimulates RUNX2 (a transcription factor for MSCs of bone marrow which leads to new bone formation).

It should be pointed out at this juncture that practically speaking all IR lasers is not pure NIR or FIR. Rather, they are typically of mixed wavelengths, with different percentages of the mixture. Therefore, the above benefits of FIR and NIR are present together and result from the application of the IR laser beam 402 to he wound 10.

As should be appreciated by those skilled in the art the subject invention provides the following benefits. It provides a faster healing process, which means reduction of time of convalescence after surgery and earlier discharge from the hospital and return to work. It is cosmetically more efficient, with less potential scarring due to the absence of fibrosis. Since the subject invention enable the production of new tissues that are similar to original ones without fibrosis, the patient should regain full function without any deformity or weakness, returning him/her to the condition before the trauma or surgery. Moreover, the subject invention enables proportionate healing, which means more new tissue formation at the area of higher stress and vice versa. This is more physiological to the organ and to its function. Postoperative operative short term and long term complications should also be greatly reduced because typically main complications are caused by fibrous tissues, e.g., post-operative hernia is more liable to occur in tissues with more fibrosis. Post-operative rupture of muscle or tendon is more liable to occur, with more fibrosis, e.g., in case of a woman having previously delivered by Caesarian section, her uterus is liable to rupture in a subsequent normal delivery at the fibrous band of previous surgery. The subject invention, by enabling better soft tissue healing, should indirectly help in faster healing of fractured bone. In this regard, recent studies show that healing of bone fracture depends on the vascular integrity of the soft tissues especially the muscles surrounding the fractured bone.

It should be pointed out at this juncture that while the above regimen, methodology and devices have focussed on orthopedic wounds, the subject invention can be used on any wound. This invention can also be used for treatment of chronic wounds that are refractory to treatment. As is known, refractory wounds, e.g., diabetic wounds, bed sores, ischemic ulcers, chronic infectious diseases, etc., usually result from either a shortage of oxygenation, excess fibrous tissue formation, and/or a lack of local energy necessary for healing. The subject invention could help in solving these problems.

Without further elaboration the foregoing will so fully illustrate our invention that others may, by applying current or future knowledge, adopt the same for use under various conditions of service.

What is claimed is:

1. A medical device, selected from the group consisting of surgical sutures, surgical staples, surgical pads, and surgical meshes, for use at a wound in a patient to facilitate the rapid healing of the tissue at the situs of the wound with minimal fibrous tissue formation, said device comprising a member arranged to be brought into engagement with tissue adjacent the wound to close the wound, said device comprising a core formed of a piezoelectric material and an outer layer covering said core, said outer layer comprising platelet derived growth factors, said platelet derived growth factors being configured to be slowly released into the substance of the wound throughout the healing process, said system also comprising a local molecular energy production agent arranged to be filled in cavities in tissue contiguous with the wound.

2. The medical device of claim 1 wherein said device is a surgical suture and wherein the diameter of said core is approximately ⅝th the diameter of said suture.

3. The medical device of claim 1 wherein said device is a surgical staple and wherein the diameter of said core is approximately ⅝th the diameter of said staple.

4. The medical device of claim 1 wherein said local molecular energy production agent comprises glutamine-creatine complex.

* * * * *